United States Patent
Lin et al.

(10) Patent No.: US 11,273,189 B2
(45) Date of Patent: Mar. 15, 2022

(54) ***LACTOBACILLUS PLANTARUM* TCI378 AND ITS USES IN LOSING FAT AND IMPROVING GASTROINTESTINAL FUNCTIONS**

(71) Applicant: TCI CO., LTD., Taipei (TW)

(72) Inventors: Yung-Hsiang Lin, Taipei (TW); Chu-Han Huang, Taipei (TW); Cheng-Yu Ho, Taipei (TW)

(73) Assignee: TCI CO., LTD, Taipei (TW)

( * ) Notice: Subject to any disclaimer, the term of this patent is extended or adjusted under 35 U.S.C. 154(b) by 43 days.

(21) Appl. No.: 16/854,676

(22) Filed: Apr. 21, 2020

(65) Prior Publication Data

US 2020/0254034 A1    Aug. 13, 2020

Related U.S. Application Data

(62) Division of application No. 15/926,413, filed on Mar. 20, 2018, now abandoned.

(60) Provisional application No. 62/473,785, filed on Mar. 20, 2017.

(51) Int. Cl.
| | |
|---|---|
| *A61K 35/747* | (2015.01) |
| *C12N 1/20* | (2006.01) |
| *C12R 1/25* | (2006.01) |
| *A23L 33/135* | (2016.01) |
| *A23K 10/18* | (2016.01) |

(52) U.S. Cl.
CPC ............ *A61K 35/747* (2013.01); *A23K 10/18* (2016.05); *A23L 33/135* (2016.08); *C12N 1/20* (2013.01); *C12N 1/205* (2021.05); *A23V 2002/00* (2013.01); *A23V 2200/3204* (2013.01); *A23Y 2220/67* (2013.01); *C12R 2001/25* (2021.05)

(58) Field of Classification Search
CPC ................................................ C12R 2001/25
See application file for complete search history.

(56) References Cited

U.S. PATENT DOCUMENTS

| | | |
|---|---|---|
| 2010/0021445 A1 | 1/2010 | Kawakami et al. |
| 2016/0058807 A1 | 3/2016 | Fukushima |
| 2017/0137902 A1 | 5/2017 | Ikenaga et al. |

FOREIGN PATENT DOCUMENTS

| | | |
|---|---|---|
| CN | 1004223 09 C | 10/2008 |
| CN | 101864375 B | 11/2011 |
| CN | 103598594 B | 5/2015 |
| CN | 104928208 A | 9/2015 |
| CN | 105105145 A | 12/2015 |
| JP | 2015-008672 A | 1/2015 |
| JP | 2015-096476 A | 5/2015 |
| KR | 10-1670048 B1 | 10/2016 |
| WO | WO 2008/108298 A1 | 9/2008 |
| WO | WO 2014/171478 A1 | 10/2014 |
| WO | WO 2015/146916 A1 | 10/2015 |

OTHER PUBLICATIONS

Park, J.-E., et al., "*Lactobacillus plantarum* LG42 isolated from gajami sik-hae decreases body and fat pad weights in diet-induced obese mice," *Journal of Applied Microbiology*, vol. 116, pp. 145-156 (2013).

*Primary Examiner* — Vera Afremova
(74) *Attorney, Agent, or Firm* — Christensen, Fonder, Dardi & Herbert PLLC

(57) ABSTRACT

*Lactobacillus plantarum* TCI378 is provided. The *Lactobacillus plantarum* TCI378 was deposited at German Collection of Microorganisms and Cell Cultures (Deutsche Sammlung von Mikroorganismen and Zellkulturen, DSMZ) under the accession number DSM 32451. A method for losing fat and/or improving gastrointestinal functions is also provided. The method comprises administering to a subject in need an effective amount of a composition, wherein the composition comprises *Lactobacillus plantarum* TCI378 and/or its metabolites.

8 Claims, 5 Drawing Sheets

Specification includes a Sequence Listing.

LACTOBACILLUS PLANTARUM TCI378 AND ITS USES IN LOSING FAT AND IMPROVING GASTROINTESTINAL FUNCTIONS

CROSS REFERENCE TO RELATED APPLICATIONS

This application is a divisional of U.S. patent application Ser. No. 15/926,413, filed Mar. 20, 2018, which claims priority to U.S. Provisional Application Ser. No. 62/473,785, filed on Mar. 20, 2017, the disclosures of which are incorporated herein in their entirety by reference.

FIELD OF THE INVENTION

The present invention relates to a novel *Lactobacillus plantarum* TCI378. The present invention also relates to the uses of *Lactobacillus plantarum* TCI378 and/or its metabolites, particularly to the uses of *Lactobacillus plantarum* TCI378 and/or its metabolites in reducing fat formation, enhancing fat metabolism and/or improving gastrointestinal functions.

BACKGROUND OF THE INVENTION

People nowadays live in a lifestyle of sleeping and waking up irregularly, seldom eating at home, suffering from high stress, and being lack of exercise, and thus, the incidence rate of metabolic syndromes, hyperglycemia, hypertension, and hyperlipidemia is getting higher and higher. It is believed that the aforementioned course starts from the weakening of gastrointestinal functions and metabolism, leading to the accumulation of daily intake calories and thus the formation of fat, thereby resulting in constipation, obesity, chronic diseases, and other symptoms or diseases which severely threaten the health of people.

Although a regular exercise and a routine consumption of vegetables can improve gastrointestinal functions and enhance fat metabolism, for those being busy and seldom eating at home, there is still a need for more convenient approaches. In the recent years, more and more products (e.g., enzymes obtained from vegetables) associated with the gastrointestinal function improvement or the enhancement of fat metabolism have been developed. Also, probiotics have become a popular target of researches.

The discussion of lipophilic probiotics had brought hope to people for using probiotics in losing fat, however, researchers thereafter indicated that none of the probiotics already discovered was able to live by degrading lipid. Some gram-negative pathogens in human gastrointestinal tract could live by degrading lipid, while too much lipid consumption would lead to a dramatic proliferation of gram-negative pathogens and the lipopolysaccharide (LPS) presenting on the surface of pathogens may induce an inflammation in human body, thereby causing obesity, diabetes mellitus, cardiovascular diseases, and even cancers.

*Lactobacillus*, which is one of probiotics presenting in human, can be used in the manufacture of various fermentation foods. There are many bacteria of genus *lactobacillus* are classified as a food additive through the GRAS process (Generally Recognized As Safe) of FDA (Food and Drug Administration).

Inventors of the present invention isolated *Lactobacillus plantarum* TCI378 and found that the strain and its metabolites are effective in reducing fat formation, enhancing fat metabolism, and improving gastrointestinal functions.

SUMMARY OF THE INVENTION

An objective of the present invention is to provide a *Lactobacillus plantarum* TCI378, which was deposited at German Collection of Microorganisms and Cell Cultures (Deutsche Sammlung von Mikroorganismen and Zellkulturen, DSMZ) under the accession number DSM 32451.

Another objective of the present invention is to provide a composition, comprising *Lactobacillus plantarum* TCI378 and its metabolites.

Still another objective of the present invention is to provide a use of *Lactobacillus plantarum* TCI378 and its metabolites in the manufacture of a composition.

The composition provided in accordance with the present invention is used for at least one of reducing fat formation, enhancing fat metabolism, blocking body fat formation, and improving gastrointestinal functions. The composition is a pharmaceutical composition, a food composition, or a feed composition. Preferably, the pharmaceutical composition is provided as a form for oral administration. The food composition is a health food, a dietary supplement, a functional food, a nutritional supplement or a special nutritional food.

Yet another objective of the present invention is to provide a method for losing fat and/or improving gastrointestinal functions, comprising administering to a subject in need an effective amount of the composition as described above.

The detailed technology and preferred embodiments implemented for the present invention are described in the following paragraphs accompanying the appended drawings for persons skilled in the art to well appreciate the features of the claimed invention.

BRIEF DESCRIPTION OF THE DRAWINGS

FIG. 2 shows, in comparison with the control group, the relative content of lipid in each other group ( presents the result is significantly different from that of the control group, $p<0.01$; ## presents the result is significantly different from that of the blank group, $p<0.01$), FIG. 3** shows, in comparison with the control group, the expression level of PLIN1 gene in the cells of each other group (* presents the result is significantly different from that of the control group, $p<0.05$;  presents the result is significantly different from that of the control group, $p<0.01$; # presents the result is significantly different from that of the blank group, $p<0.05$), FIG. 4 shows, in comparison with the control group, the expression level of GLUT4 gene in the cells of each other group ( presents the result is significantly different from that of the control group, $p<0.01$; # presents the result is significantly different from that of the blank group, $p<0.05$), and wherein, the cells in control group were cultivated in an adipocyte maintenance medium, those in the blank group were cultivated in an adipocyte maintenance medium containing 1% MRS broth, and those in the TCI378 group were cultivated in an adipocyte maintenance medium containing 1% TCI378 sample;

5 shows whole-body fat percentage (* presents the result is significantly different from that of the $0^{th}$ day, p<0.05), FIG. 6 shows trunk fat percentage (* presents the result is significantly different from that of the $0^{th}$ day, p<0.05), FIG. 7 shows body weight (** presents the result is significantly different from that of the 0th day, p<0.01), FIG. 8 shows waist circumference (* presents the result is significantly different from that of the $0^{th}$ day, p<0.05), and FIG. 9 shows BMI value (**presents the result is significantly different from that of the 0th day, p<0.01);

DESCRIPTION OF THE PREFERRED EMBODIMENT

Figure 1:
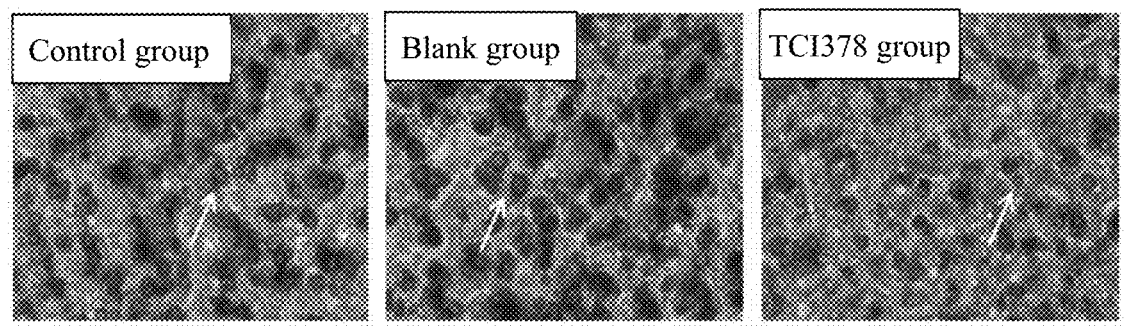
FIGS. 1 to 4 show the results of adipocytes being treated with different media, wherein FIG. 1 are photographs showing the cells being treated and stained (the dark zones pointed by arrows are oil droplets)

The following paragraphs will describe some of the embodiments of the present invention in detail. However, without departing from the spirit of the present invention, the present invention may be embodied in various embodiments and should not be limited to the embodiments described in the specification. Unless otherwise indicated herein, the expression "a," "an," "the," or the like recited in the specification of the present invention (especially in the claims) are intended to include both the singular and plural forms; the term "subject" recited in this specification refers to an animal, including mammalian (e.g., human), or non-mammalian (e.g., fowl or bird).

Inventors of the present invention isolated a novel strain from kimchi, analyzed the strain by 16S rRNA gene sequence analysis, and identified the strain as a *Lactobacillus plantarum* based on the phylogenetic relationship, and thus, named the strain as *Lactobacillus plantarum* TCI378. *Lactobacillus plantarum* TCI378 has been deposited at German Collection of Microorganisms and Cell Cultures (Deutsche Sammlung von Mikroorganismen and Zellkulturen, DSMZ) under the accession number DSM 32451. The *Lactobacillus plantarum* TCI378 has a 16S rRNA fragment of SEQ ID NO: 1.

Inventors of the present invention found that *Lactobacillus plantarum* TCI378 and its metabolites are effective in reducing fat formation, enhancing fat metabolism, and improving gastrointestinal functions. Therefore, the present invention provides a *Lactobacillus plantarum* TCI378, a composition comprising *Lactobacillus plantarum* TCI378 and/or its metabolites, and a use of *Lactobacillus plantarum* TCI378 and/or its metabolites in the manufacture of a composition, wherein the composition is used for at least one of reducing fat formation, enhancing fat metabolism, blocking body fat formation and improving gastrointestinal functions.

The metabolites of *Lactobacillus plantarum* TCI378 adopted in accordance with the present invention could be generated by cultivating *Lactobacillus plantarum* TCI378 under an environment suitable for its growth. For example, a *Lactobacillus plantarum* TCI378's metabolites-containing liquid could be obtained by cultivating *Lactobacillus plantarum* TCI378 in a suitable medium, and then optionally removing the solids, including bacteria, from the medium.

To provide the desired metabolites, any suitable medium could be chosen and used to perform the cultivation of *Lactobacillus plantarum* TCI378, as long as the medium can provide the desired nutrients (e.g., yeast extract, protein and glucose) and conditions (e.g., pH value) for the growth and metabolism of *Lactobacillus plantarum* TCI378. Furthermore, the time period for cultivating *Lactobacillus plantarum* TCI378 is not specifically limited, as long as the time period is sufficient for the *Lactobacillus plantarum* TCI378 to complete at least one metabolic cycle. For example, in one embodiment of the present invention, *Lactobacillus plantarum* TCI378 was cultivated in a MRS broth for 18 hours to let the strain metabolize and generate metabolites.

The present invention could directly use a medium that has undergone the metabolic cycles of *Lactobacillus plantarum* TCI378, which contains the *Lactobacillus plantarum* TCI378 and its metabolites. Otherwise, the present invention could use a *Lactobacillus plantarum* TCI378's metabolites-containing liquid, from which the solids such as *Lactobacillus plantarum* TCI378 have been removed. Any suitable procedure could be employed to remove the solids, as long as the procedure does not adversely affect the desired effects of the metabolites generated after cultivation. Generally, physical approaches, such as centrifugal separation, filter filtration, precipitation and decantation, could be employed to remove the solids. Optionally, the above procedures could be repeated or combined to remove solids (including bacteria) from the medium as much as possible.

Depending on the desired purpose, the pharmaceutical composition in accordance with the present invention could be provided in any suitable form without special limitations. For example, the pharmaceutical composition could be administered to a subject in need by an oral administration. Depending on the form and purpose, suitable carriers could be chosen and used to provide the pharmaceutical composition, wherein the carriers include excipients, diluents, auxiliaries, stabilizers, absorbent retarders, disintegrating agents, hydrotropic agents, emulsifiers, antioxidants, adhesives, binders, tackifiers, dispersants, suspending agents, lubricants, hygroscopic agents, etc.

As a dosage form for oral administration, the pharmaceutical composition provided in accordance with the present invention could comprise any pharmaceutically acceptable carrier that will not adversely affect the desired effects of the active ingredients (i.e., *Lactobacillus plantarum* TCI378 and its metabolites). Examples of suitable carriers include, but is not limited to, water, saline, dextrose, glycerol, ethanol or its analogs, cellulose, starch, sugar bentonite, and combinations thereof. The pharmaceutical composition could be provided in any suitable form for oral administration, such as in a form of a tablet (e.g., dragees), a pill, a capsule, granules, a pulvis, a fluidextract, a solution, a syrup, a suspension, a tincture, etc.

Depending on the need, age, body weight, and health conditions of the subject, the pharmaceutical composition provided in accordance with the present invention could be administered at various frequencies, such as once a day, multiple times a day, or once every few days, etc. The ratio of amount of *Lactobacillus plantarum* TCI378 and/or its metabolites in the pharmaceutical composition provided in accordance with the present invention could be adjusted depending on the requirements of practical application. In addition, the pharmaceutical composition could optionally further comprise one or more other active ingredient(s), or to be used in combination with a medicament comprising one or more other active ingredient(s), to further enhance the effects of the pharmaceutical composition, or to increase the application flexibility and application adaptability of preparation thus provided, as long as the other active ingredients do not adversely affect the desired effects of the active ingredients of the present invention (i.e., *Lactobacillus plantarum* TCI378 and its metabolites).

The food composition provided in accordance with the present invention could be a health food, a daily supplement, a functional food, a nutritional supplement, or a special nutritional food, and could be manufactured as dairy products, meat products, breads, pasta, cookies, troche, capsule, fruit juices, teas, sport drinks, nutritional drinks, etc., but is not limited thereby.

Depending on the need, age, body weight and health conditions of the subject, the health food, daily supplement, functional food, nutritional supplement, and special nutritional food provided in accordance with the present invention could be taken at various frequencies, such as once a day, multiple times a day, or once every few days, etc. The amount of *Lactobacillus plantarum* TCI378 and/or its metabolites in the health food, daily supplement, functional food, nutritional supplement, and special nutritional food provided in accordance with the present invention could be adjusted, preferably to the amount that it should be taken daily, depending on the specific population.

The recommended daily dosage, use standards and use conditions for a specific population (e.g., patients suffering from hyperlipidemia, pregnant woman, etc.), or the recommendations for a use in combination with another food product or medicament could be indicated on the exterior package of the health food, daily supplement, functional food, nutritional supplement, and/or special nutritional food provided in accordance with the present invention. Thus, it is suitable for the user to take the health food, daily supplement, functional food, nutritional supplement, and/or special nutritional food by him- or herself safely and securely without the instructions of a doctor, pharmacist, or related executive. In the food composition provided in accordance with the present invention, the types of *Lactobacillus plantarum* TCI378 and/or its metabolites are in line with the above descriptions.

Optionally, the pharmaceutical composition, food composition, or feed composition provided in accordance with the present invention could further comprise a suitable amount of additives, such as a flavoring agent, a toner, or a coloring agent for enhancing the palatability and the visual perception of the pharmaceutical composition, food composition, or feed composition, and/or a buffer, a conservative, a preservative, an antibacterial agent, or an antifungal agent for improving the stability and storability of the pharmaceutical composition, food composition, or feed composition.

The present invention also provides a method for reducing fat formation, enhancing fat metabolism, blocking body fat formation, and/or improving gastrointestinal functions, comprising administering to a subject in need an effective amount of a composition, wherein the composition comprises *Lactobacillus plantarum* TCI378 and/or its metabolites. The types of *Lactobacillus plantarum* TCI378 and/or its metabolites are also in line with the above descriptions.

The present invention will be further illustrated in detail with specific examples as follows. However, the following examples are provided only for illustrating the present invention and the scope of the present invention is not limited thereby. The scope of the present invention will be indicated in the appended claims.

EXAMPLES

Preparation Examples

A. Selection and Identification of *Lactobacillus plantarum* TCI378

(A-1) Selection

The homogenate of kimchi (including kimchi and souse) was mixed with a MRS broth at a volume ratio of kimchi: MRS broth=1:100, and then the mixture thus provided was subjected to an anaerobic cultivation (i.e., the oxygen concentration is less than 5%) at a temperature of 37° C. for 18 hours. Thereafter, the cultivated mixture was spread onto a MSR agar, and then the agar was subjected to an anaerobic cultivation at 37° C., to form different colonies on the agar. Then, to confirm the uniqueness of the strain, a colony was picked up by using a sterilized inoculating loop and subjected to the quadrant streaking method on a MSR agar, and then, the MSR agar was incubated in an anaerobic incubator at 37° C. until single colony appeared.

(A-2) Identification

The strain selected from (A-1) was subjected to a phylogenetic analysis, and it was confirmed that the strain has a 16S rRNA fragment with a sequence as shown in SEQ ID NO: 1. SEQ ID NO: 1 was compared to the online database of National Center for Biotechnology Information (NCBI), and it was noted that SEQ ID NO: 1 has an identity of about 99% to the 16S rRNA fragment of *Lactobacillus plantarum* strain. Hence, depending on the phylogenetic identification, the strain selected from (A-1) was identified as a *Lactobacillus plantarum* strain according to the phylogenetic relationship and was named as *Lactobacillus plantarum* TCI378.

(A-3) Storage

The unique strain obtained from (A-1) was subjected to a liquid cultivation with a MRS broth to provide a bacteria cultivation liquid. Thereafter, glycerol was added into the bacteria cultivation liquid at a volume ratio of glycerol: bacteria cultivation liquid=1:3 to provide a mixture, and then, the mixture was placed into collection tubes and stored at a temperature of −80° C.

B. *Lactobacillus plantarum* TCI378 Activation and Sample Preparation (B-1) Activation The collection tube containing *Lactobacillus plantarum* TCI378 was thawed, and then TCI378 strain was inoculated into a MRS broth at an inoculum concentration of 1% (about $1 \times 10^4$ CFU/mL) and cultivated under an anaerobic condition at 37° C. for 18 hours, so as to provide a TCI378 cultivation liquid for use in the following experiments.

(B-2) Sample Preparation

The TCI378 cultivation liquid obtained from (B-1) was inoculated into a MRS broth at an inoculum concentration of 1% (about $1 \times 10^4$ CFU/mL) and cultivated under an anaerobic condition at 37° C. for 18 hours. After the aforementioned cultivation, the broth was subjected to a centrifugation at a speed of 5,000 rpm for 5 minutes to remove the bacteria (i.e., TCI378 strain). And then, the supernatant of the centrifuged medium was filtered with a 0.2 μm filter to further remove the bacteria. The filtrate was collected form the filtration, and a TCI378 sample (containing metabolites of *Lactobacillus plantarum* TCI378) was thus obtained.

C. Cultivation of Adipocytes (C-1) Medium (1) Pre-Adipocyte Expansion Medium:

90% Dulbecco's Modified Eagle's Medium (DMEM; purchased from Gibco);

10% Bovine Serum (purchased from Gibco); and
1% Penicillin-streptomycin (purchased from Gibco).

(2) Differentiation Medium:
90% Dulbecco's Modified Eagle's Medium (DMEM; purchased from Gibco);
10% Fetal Bovine Serum (purchased from Gibco);
1% Penicillin-streptomycin (purchased from Gibco);
1.0 μmole/mL Dexamethasone (purchased from Sigma);
0.5 mmole/mL Methylisobutylxanthine (purchased from Sigma); and
1.0 μg/mL insulin (purchased from Sigma).

(3) Adipocyte Maintenance Medium:
90% Dulbecco's Modified Eagle's Medium (DMEM; purchased from Gibco);
10% Fetal Bovine Serum (purchased from Gibco);
1% Penicillin-streptomycin (purchased from Gibco); and
1.0 μg/mL insulin (purchased from Sigma).

(C-2) Differentiation of Adipocytes

A 24-well plate was injected with the Pre-adipocyte expansion medium of (C-1) in each well, and then, the mouse 3T3-L1 fibroblasts (purchased from Food Industry Research and Development Institute, BCRC 60071) were seeded into a 24-well plate at a seeding density of $8\times10^4$ cells/well and cultivated at 37° C. for 48 hours. Thereafter, the medium was replaced by the differentiation medium of (C-1) and the cultivation was continued for 4 days at 37° C. And then, the medium was further replaced by the adipocyte maintenance medium of (C-1) and the cultivation was continued for 8 days at 37° C., so as to provide adipocytes for use in the following experiments.

Example 1: Effects of *Lactobacillus plantarum* TCI378 and its Metabolites on Losing Fat (1-1) Cell Treatment The adipocytes obtained from [Preparation example C-2] were divided into three groups, and separately cultivated with the following media at 37° C. for 48 hours:

| Group | Condition of the medium |
|---|---|
| Control group | adipocyte maintenance medium |
| Blank group | adipocyte maintenance medium + 1% MRS broth |
| TCI378 group | adipocyte maintenance medium + 1% TCI378 sample |

(1-2) Lipid (Oil Red O) Staining

The cells of each group obtained from the cultivation of (1-1) were washed with phosphate-buffered saline (PBS) twice, and then, 1 mL of 10% methanol was added into each group to provide a mixture, and the mixture was placed at room temperature for 30 minutes to fix cells. Then, the methanol was removed and the cells were washed with PBS twice. 1 mL of 50% isopropanol was added into each group for 1 minute, and then removed. Finally, oil red O solution was added into each group and incubated at room temperature for 1 hour to stain the oil droplet of cells. The oil red O solution was removed, and the cells were washed with PBS twice. Then, the oil droplets of adipocytes were observed under a microscope and pictures were taken. The results are shown in FIG. 1 (the dark zones pointed by arrows are oil droplets).

Figure 2:
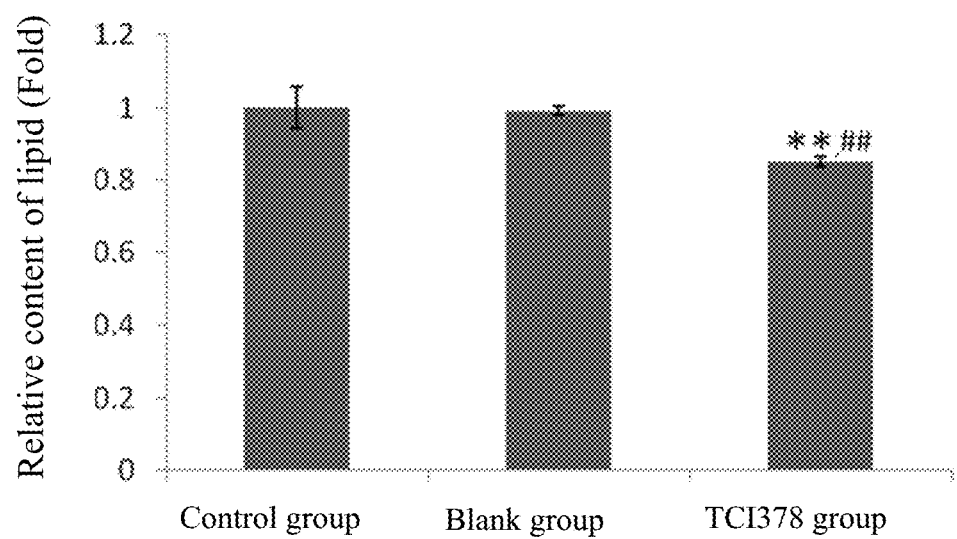

After the above observation and recording of oil droplets were completed, the cells in each group were treated with 100% isopropanol for 10 minutes to dissolve the accumulated oil droplets. And then, cells in each group was subjected to an absorbance measurement at a wavelength of 510 nm to determine the content of lipid in the cells of each group. Finally, the relative content of lipid in the cells of blank group and TCI378 group was respectively calculated by using the result of control group as a basis (i.e., set the content of lipid in the control group as 1-fold). The results are shown in FIG. 2.

As shown in FIG. 1, in comparison with the control group, the oil droplets in the TCI378 group were smaller, while the oil droplets in the blank group did not change significantly. As shown in FIG. 2, no matter in comparison with the control group and blank group, the relative content of lipid in the cells of TCI378 group was decreased about 15%. These results indicate that *Lactobacillus plantarum* TCI378 and its metabolites are effective in decreasing the content of lipid in adipocytes.

(1-3) Analysis of Gene Expression

It is known that the protein, Perilipin, can protect the oil droplets of adipocytes from destruction. If the expression level of Perilipin can be decreased, the oil droplets of adipocytes will be destroyed more easily, thereby the fat metabolism can be enhanced. It is also known that the increased expression of GLUT4 gene will affect the ability of adipocytes on absorbing glucose, thereby leading to the production of fatty acids and causing obesity. Therefore, if the expression level of GLUT4 gene can be decreased, the fat formation will be reduced. To confirm whether *Lactobacillus plantarum* TCI378 and its metabolites have effects on enhancing fat metabolism and/or reducing fat formation, the following analysis were conducted to investigate the influences of *Lactobacillus plantarum* TCI378 and its metabolites on the expression levels of PLIN1 (i.e., the gene which expresses Perilipin) and GLUT4 genes.

The cells of each group provided by (1-1) were harvested and subjected to a RNA extraction with an RNA purification kit (purchased from GeneMark). Then, the RNA was retro-transcribed into cDNA by using a SuperScript™ Reverse Transcriptase kit (purchased from Invitrogen). Thereafter, the cDNA was subjected to a quantitative polymerase chain reaction (qPCR) by using a SYBR Green Master Mix (purchased from KAPA) and ABI StepOne Plus' System to determine the expression levels of PLIN1 and GLUT4 genes in the cells of each group. Then, the relative expression level of PLIN1 and GLUT4 genes of the TCI378 group were calculated by using the result of the control group as a basis (i.e., set the expression level of the control group as 1-fold). The results are shown in FIG. 3 and FIG. 4.

Figure 3:
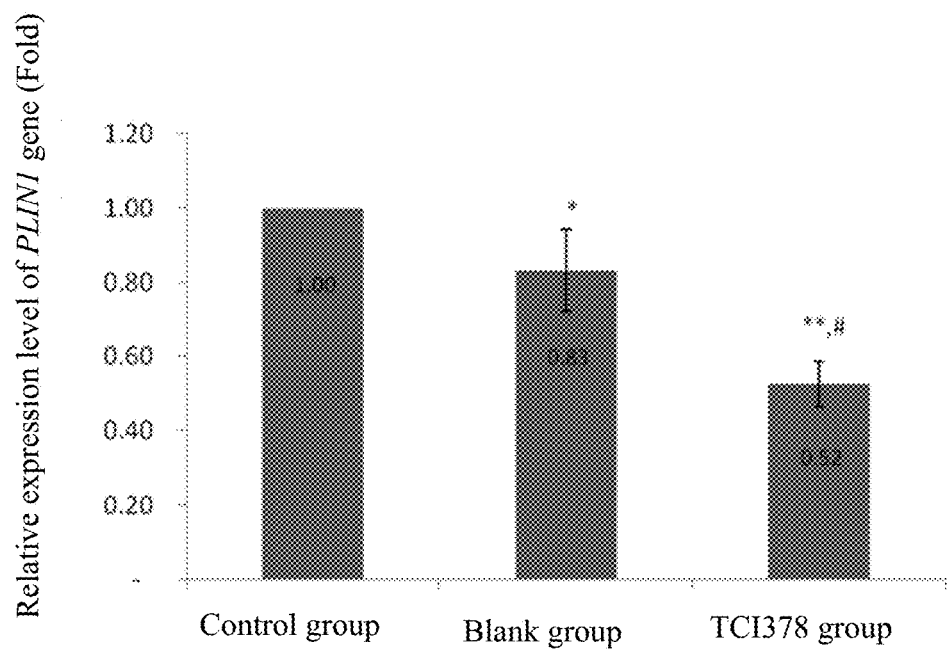
Figure 4:
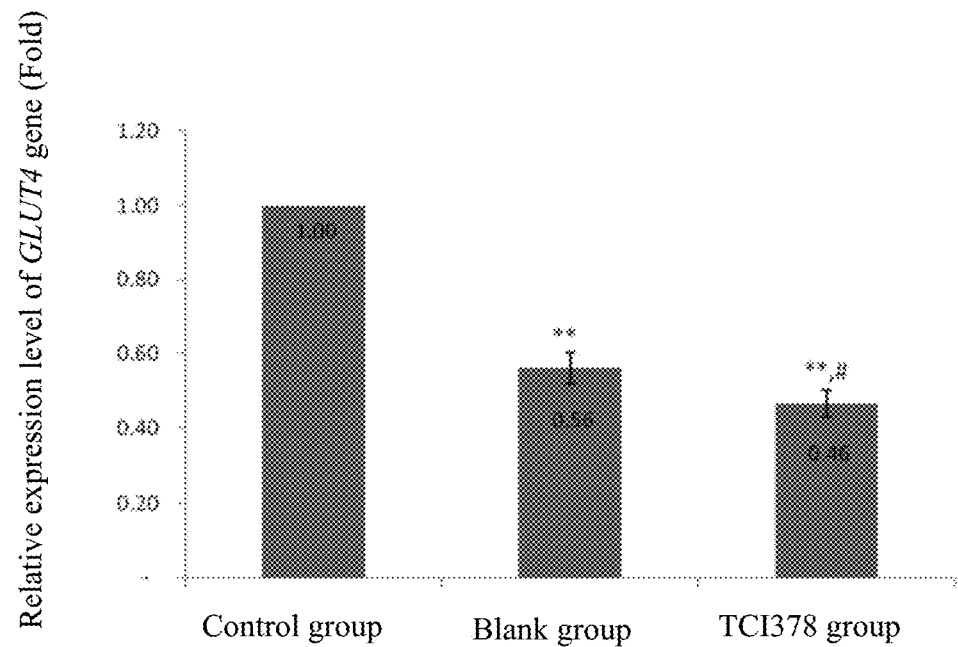
Figure 5:
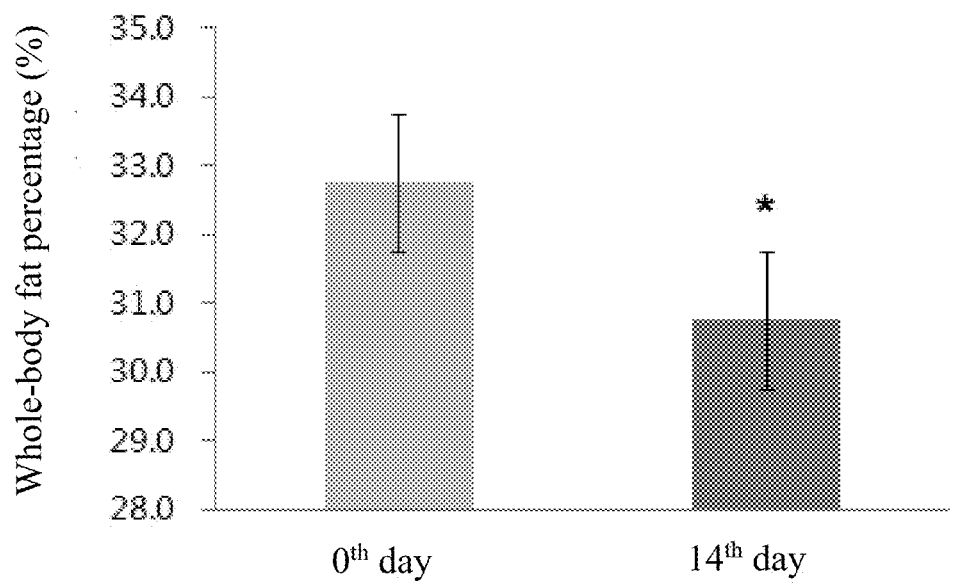
FIGS. 5 to 9 illustrate the effects of *Lactobacillus plantarum* TCI378 on losing fat by comparing the indicators of subjects at the 0th day (i.e., prior to taking capsules containing *Lactobacillus plantarum* TCI378) and at the 14$^{th}$ day (i.e., after taking a capsule containing *Lactobacillus plantarum* TCI378 per day for 14 consecutive days), wherein FIG.
Figure 6:
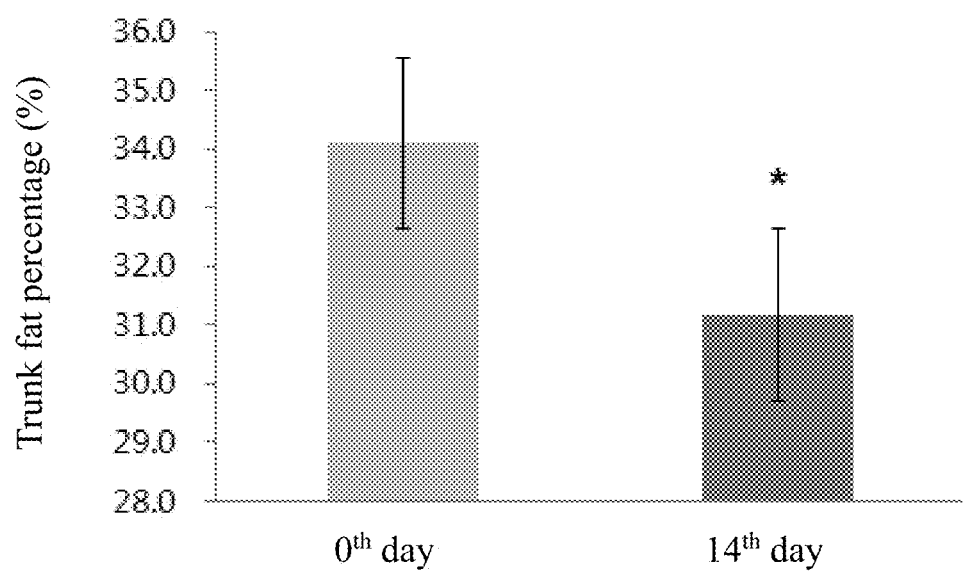
Figure 7:
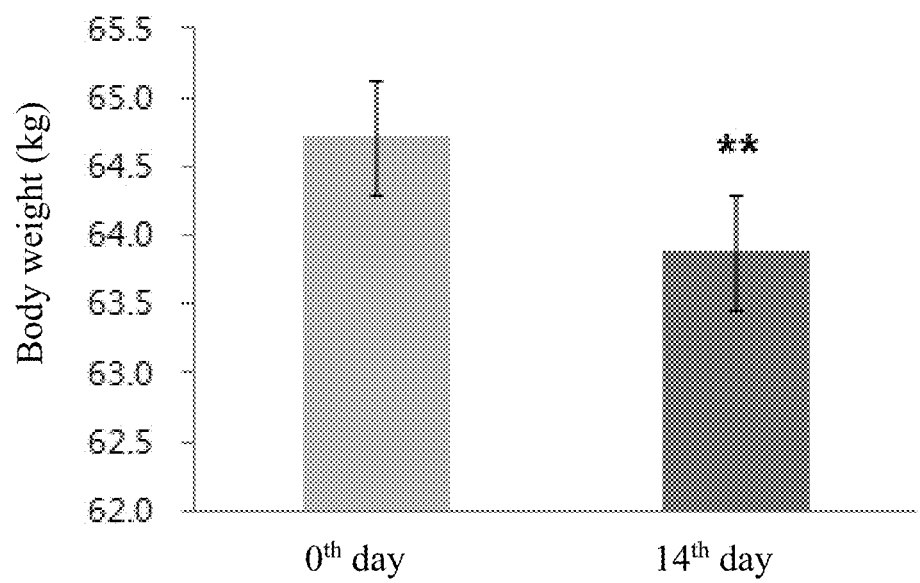
Figure 8:
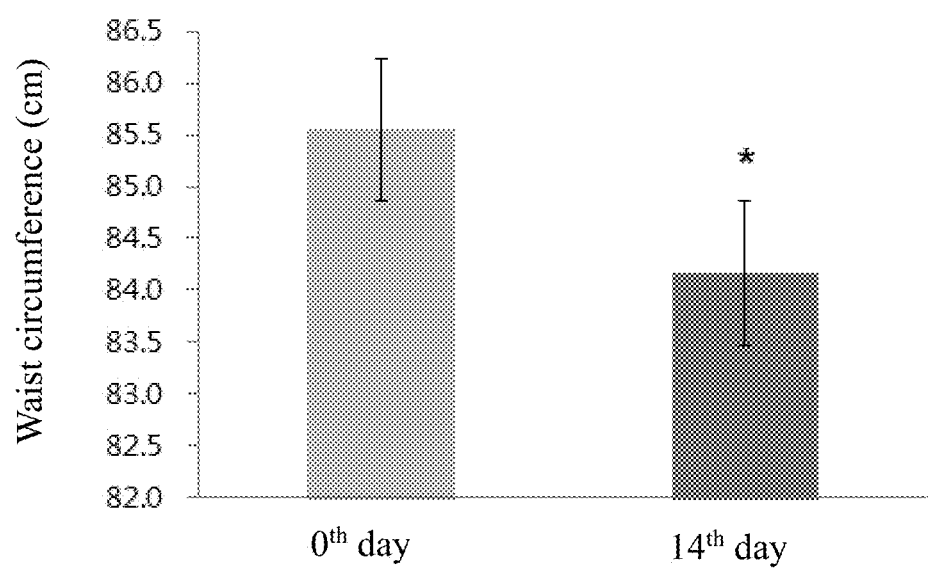
Figure 9:
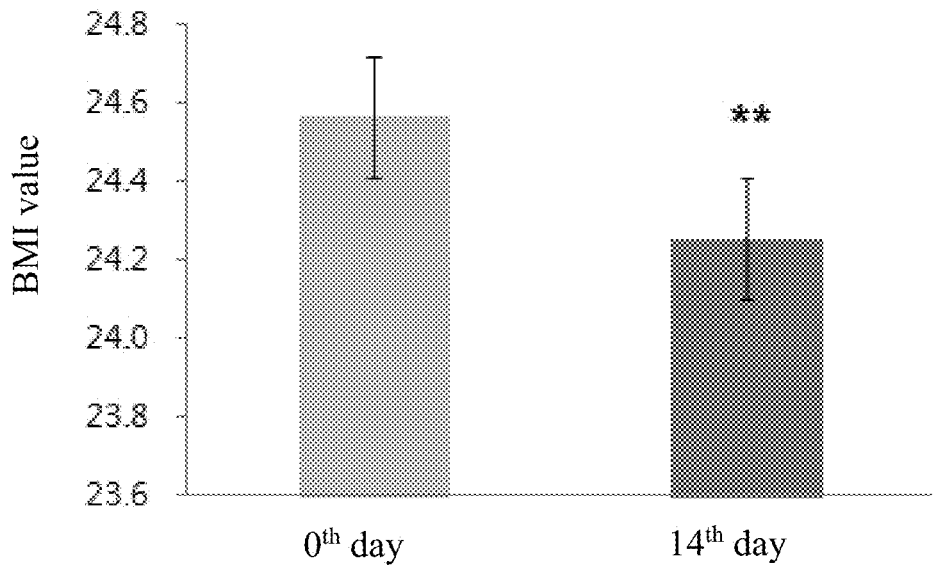

As shown in FIG. 3 and FIG. 4, no matter in comparison with the control group and blank group, the expression levels of PLIN1 and GLUT4 genes in the TCI378 group were significantly lower.

The results of (1-2) and (1-3) indicate that *Lactobacillus plantarum* TCI378 and its metabolites in accordance with the present invention are effective in reducing fat formation and enhancing fat metabolism, and thus can be used for decreasing the content of lipid in adipocytes, thereby blocking body fat formation.

Example 2: Effects of *Lactobacillus plantarum* TCI378 on Losing Fat and Improving Gastrointestinal Functions Ten volunteered subjects, who have a body fat percentage more than 27% and did not take any diet foods or drugs, were recruited. Prior to conducting the experiment (i.e., before taking the capsule containing *Lactobacillus plantarum* TCI378), each subject was invited to self-evaluate the frequency of feeling incomplete bowel movement (selecting one form the group consisting of "never," "often," "sometimes," and "always"), and measure the body weight, waist circumference, BMI value, whole-body fat percentage, and trunk fat percentage. Then, each subject took a capsule containing *Lactobacillus plantarum* TCI378 (5×10$^9$ CFU/capsule) a day for 14 consecutive days (i.e., each subject took the capsule 14 times). Thereafter, each subject was again invited to self-evaluate the frequency of feeling incomplete bowel movement, and measured the body weight, waist circumference, BMI value, whole-body fat percentage, and trunk fat percentage. Finally, the whole-body fat percentage, trunk fat percentage, body weight, waist circumference and BMI value of the ten subjects were averaged and shown in FIG. 5 to FIG. 9 respectively. In addition, a statistical analysis was conducted on the self-evaluation results of feeling incomplete bowel movement, and the ratio of subjects "never," "often," "sometimes," and "always" feeling incomplete bowel movement was respectively calculated by setting the total number of subjects as "1". The result shows in FIG. 10.

Figure 10:
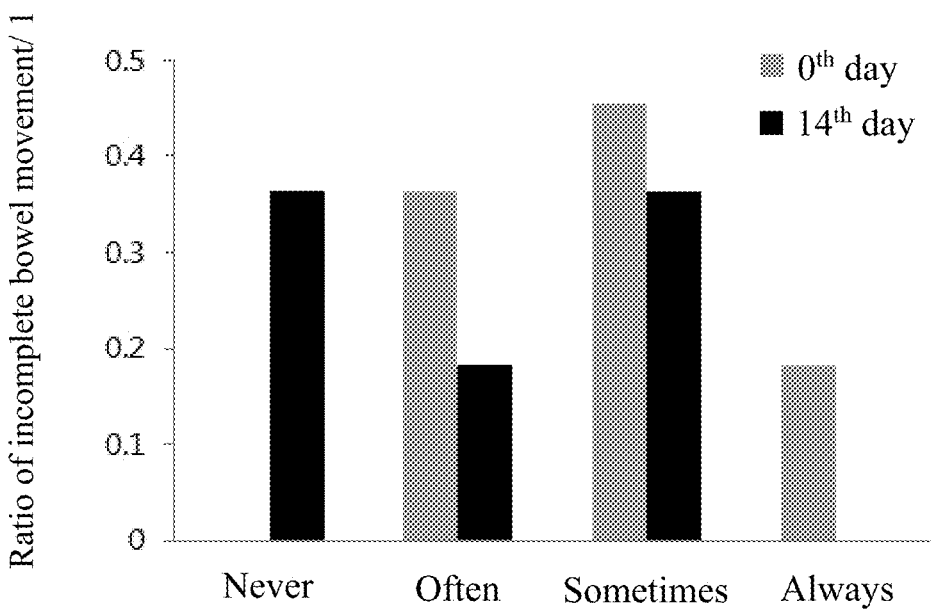
FIG. 10 shows the defecation frequency of the subjects at the $0^{th}$ day and at the $14^{th}$ day, and thus illustrates the effects of *Lactobacillus plantarum* TCI378 on improving gastrointestinal functions.

As shown in FIG. 5 to FIG. 9, in comparison with those at the 0th day (i.e., prior to taking the capsule containing *Lactobacillus plantarum* TCI378), both whole-body fat percentage and trunk fat percentage were significantly decreased at the 14$^{th}$ day (i.e., after taking the capsule containing *Lactobacillus plantarum* TCI378 for 14 consecutive days). In comparison with those at the 0th day, the body weight, waist circumference and BMI value were also decreased at the 14$^{th}$ day. In addition, as shown in FIG. 10, the frequency of feeling incomplete bowel movement was reduced after the subjects took the capsule containing *Lactobacillus plantarum* TCI378 for 14 consecutive days.

The above results show that, after the subjects took the capsule containing *Lactobacillus plantarum* TCI378, their fat accumulation and gastrointestinal functions are both improved, and their body weight, BMI value and waist circumference were decreased thereby. Therefore, the *Lactobacillus plantarum* TCI378 and its metabolites provided in accordance with the present invention can be used for at least one of reducing fat formation, enhancing fat metabolism, blocking body fat formation, and improving gastrointestinal functions.

DEPOSIT OF BIOLOGICAL MATERIAL

Depository institute: German Collection of Microorganisms and Cell Cultures (Deutsche Sammlung von Mikroorganismen and Zellkulturen, DSMZ)
Address: Inhoffenstraße 7 B, 38124 Braunschweig, GERMANY
Date: 2017 Mar. 13
Deposited biological material: *Lactobacillus plantarum* TCI378
Accession number: DSM32451

What is claimed is:

1. A method for losing fat, comprising administering to a subject in need thereof an effective amount of a composition comprising a *Lactobacillus plantarum* TCI378 and/or its metabolites, wherein the *Lactobacillus plantarum* TCI378 was deposited at German Collection of Microorganisms and Cell Cultures (Deutsche Sammlung von Mikroorganismen and Zellkulturen, DSMZ) under the accession number DSM 32451, and the metabolites is obtained by cultivating *Lactobacillus plantarum* TCI378 in a medium.

2. The method as claimed in claim 1, wherein the composition is administered to the subject as a pharmaceutical composition, a food composition, or a feed composition, thereby achieving at least one of reducing fatty acid production, enhancing fat metabolism, blocking body fat formation, and improving gastrointestinal functions.

3. The method as claimed in claim 2, wherein the composition is administered to the subject as a pharmaceutical composition.

4. The method as claimed in claim 3, wherein the pharmaceutical composition is administered to the subject by oral administration.

5. A method for improving gastrointestinal functions, comprising administering to a subject thereof in need an effective amount of the composition as claimed in claim 1.

6. The method as claimed in claim 5, wherein the composition is administered to the subject as a pharmaceutical composition, a food composition, or a feed composition, thereby relieving incomplete bowel movement.

7. The method as claimed in claim 6, wherein the composition is administered to the subject as a pharmaceutical composition.

8. The method as claimed in claim 7, wherein the pharmaceutical composition is administered to the subject by oral administration.

* * * * *

SEQUENCE LISTING

```
<160> NUMBER OF SEQ ID NOS: 1

<210> SEQ ID NO 1
<211> LENGTH: 1076
<212> TYPE: DNA
<213> ORGANISM: Lactobacillus plantarum
<220> FEATURE:
<223> OTHER INFORMATION: 16S rRNA fragment
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (184)..(184)
<223> OTHER INFORMATION: n is a, c, g, or t

<400> SEQUENCE: 1
gctggcggcg tgctatacat gcagtcgaac gaactctggt attgattggt gcttgcatca      60
tgatttacat ttgagtgagt ggcgaactgg tgagtaacac gtgggaaacc tgcccagnag    120 cggggataa  cacctggaaa cagatgctaa taccgcataa caacttggac cgcatggtcc    180
gagnttgaaa gatggcttcg gctatcactt ttggatggtc ccgcggcgta ttagctagat    240
ggtggggtaa cggctcacca tggcaatgat acgtagccga cctgagaggg taatcggcca    300
cattgggact gagacacggc ccaaactcct acggaggca gcagtaggga atcttccaca     360
atggacgaaa gtctgatgga gcaacgccgc gtgagtgaag aagggtttcg gctcgtaaaa    420
ctctgttgtt aaagaagaac atatctgaga gtaactgttc aggtattgac ggtatttaac    480
cagaaagcca cggctaacta cgtgccagca gccgcggtaa tacgtaggtg gcaagcgttg    540
tccggattta ttgggcgtaa agcgagcgca ggcggttttt taagtctgat gtgaaagcct    600
tcggctcaac cgaagaagtg catcggaaac tgggaaactt gagtgcagaa gaggacagtg    660
gaactccatg tgtagcggtg aaatgcgtag atatatggaa gaacaccagt ggcgaaggcg    720
```

-continued

```
gctgtctggt ctgtaactga cgctgaggct cgaaagtatg ggtagcaaac aggattagat    780
accctggtag tccataccgt aaacgatgaa tgctaagtgt tggagggttt ccgcccttca    840
gtgctgcagc taacgcatta agcattccgc ctggggagta cggccgcaag gctgaaactc    900
aaaggaattg acgggggccc gcacaagcgg tggagcatgt ggtttaattc gaagctacgc    960
gaagaacctt accaggtctt gacatactat gcaaatctaa gagattagac gttcccttcg   1020
ggacatggat acaggtggtg catggttgtc gtcagctcgt gtcgtgagat gttggg       1076
```